US006432682B1

(12) United States Patent
Omura et al.

(10) Patent No.: US 6,432,682 B1
(45) Date of Patent: Aug. 13, 2002

(54) SUBSTANCES KF-1040 AND PROCESS FOR PRODUCING OF THE SAME

(75) Inventors: Satoshi Omura; Hiroshi Tomoda; Rokuro Masuma, all of Tokyo (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 09/581,660

(22) PCT Filed: Feb. 16, 1998

(86) PCT No.: PCT/JP98/00614

§ 371 (c)(1),
(2), (4) Date: Aug. 8, 2000

(87) PCT Pub. No.: WO99/41265

PCT Pub. Date: Aug. 19, 1999

(51) Int. Cl.$^7$ .............................. C12P 19/44; C12N 1/00; A61K 31/70; C07H 15/00
(52) U.S. Cl. ........................... 435/74; 435/822; 514/25; 536/4.1
(58) Field of Search .............................. 536/4.1; 435/74, 435/822; 514/25

(56) References Cited

U.S. PATENT DOCUMENTS 4,814,324 A  3/1989  Borris et al.

FOREIGN PATENT DOCUMENTS

JP   4-360894   12/1992

OTHER PUBLICATIONS

Tomoda Et Al, The Journal of Antibiotics, vol. 45 No. 8 pp. 1202–1206, Aug. 1992.*
Tomoda Et Al, The Journal of Antibiotics, vol. 52, No. 8, pp. 689–694, Aug. 1999.*
Tasuda Et Al, The Journal of Antibiotics, vol. 52, No. 9, pp. 815–826, Sep. 1999.*

Y.A. Hannun, "The Sphingomyelin Cycle and the Second Messenger Function of Ceramide," The Journal of Biochemical Chemistry, vol. 269, No. 5, Feb. 4, 1994, pp. 3125–3128.
R. Kolesnick et al., "Sphingomyelin Pathway in Tumor Necrosis Factor and Interleukin–1 Signaling," Cell, vol. 77, May 6, 1994, pp. 325–328.
L.M. Boucher et al., "CD28 Signals through Acidic Sphingomyelinase," J. Exp. Med, vol. 181, Jun. 1995, pp. 2059–2068.
Medicine Immunology, vol. 28, No. 3, 1994, pp. 397–401.
N. Mayorek et al., "Inhibition of Diacylglycerol Acyltransferase by 2–Bromooctanoate in Cultured Rat Hepatocytes," The Journal of Biological Chemistry, vol. 260, No. 11, 1985, pp. 6528–6532.
H. Tomoda et al., "Evidence for an Essential Role of Long Chain Acyl–CoA Synthetase in Animal Cell Proliferation," The Journal of Biological Chemistry, vol. 266, No. 7, 1991, pp. 4214–4219.
E.N. Maruyama et al., "Purification and Characterization of Neutral and Acid Sphingomyelinases from Rat Brain," Journal of Neurochemistry, vol. 52, No. 2, 1989, pp. 611–618.
CS Jones et al., "Purification of sphingomyelinase to apparent homogeneity by using hydrophobic chromatography," Biochem. J., May 1, 1981.

* cited by examiner

Primary Examiner—Elli Peselev
(74) Attorney, Agent, or Firm—Young & Thompson

(57) ABSTRACT

A process for producing a substance KF-1040A represented by formula (I), and another substance KF-1040B represented by formula (II), which comprises culturing microorganisms capable of producing the substances KF-1040A and KF-1040B, thus accumulating these KF-1040A and/or KF-1040B in the liquid culture and harvesting the same from the culture. Because of the activities of inhibiting diacyloglycerol transferase and sphingomyelinase, the above substances are useful in preventing and treating arteriosclerosis, obesity, thrombus, inflammation and immune function-related diseases.

9 Claims, 8 Drawing Sheets

SUBSTANCES KF-1040 AND PROCESS FOR PRODUCING OF THE SAME

This application is a 371 of PCT/JP98/00617 filed Feb. 19, 1998.

FIELD OF THE INVENTION

The present invention relates to novel KF-1040 substance having an inhibitory activity for lipid metabolism as well as to a process for producing such substance.

PRIOR ARTS

There have been known anti-obesity drugs and drugs for hyperlipidemia. For example, centrally acting anorectics will suppress appetite, which may, however, be harmful for health due to reduction of appetite. Therefore, it has been expected to develop a new anti-obesity drug or a therapeutic drug for hyperlipidemia which reveals no side effect.

On the other hand, it has recently been made clear that hydrolysis of sphingomyelin which is one of lipids constituting a biomembrane has involved in the intracellular signal transduction by cytokine, such as interleukin 1β or tumor necrosis factor α [Y. A. Hannun, J. Biol. Chem., 269, 3125–3128 (1994) and R. Kolesnick & D. W. Golde, Cell, 77, 325–328 (1994)], and in the intracellular signal transduction upon activation of T cells [L. M. Boucher et al, J. Exp. Med., 18, 2059–2068 (1995) and A. Ochi, Medicinal Immunol., 28, 397–401 (1994)] and has a function in the diseases such as arteriosclerosis, inflammations, thrombosis and so on and in the immunoregulation mechanisms therefor. However, any prophylactic or therapeutic medicament for these diseases has not yet been developed in practice from a standpoint of the specific and potential inhibit or for sphingomyelinase, a hydrolase of sphingomyelin.

Problem to be Solved by the Invention

In recent years, increase in the population of patients with life-style related diseases has brought about large problems in the therapeutic and preventive medical sciences. Especially, diseases of obesity and hyperlipidemia by accumulation of triacylglycerols due to recent habit of luxurious diet may often lead to more serious diseases such as arteriosclerosis, fatty liver, hypertension, diabetes, coronary heart disease, stroke, gallbladder disease, osteoarthritis, respiratory problems and some types of cancer.

Obesity refers to a physical state in which the stored fat, constituted mainly of triglycerides, is accumulated excessively in the body, ascribed to an increased synthesis of triacylglycerols causing extraneous accumulation of fat in the adipose tissue. Also triacylglycerolaemia is believed to be triggered by facilitation of triacylglycerol synthesis in intestine and in liver causing, thus, a lipoproteineamia with a high concentration of triacylglycerols in blood. Therefore, it is assumed that any substance exhibiting an inhibitory action onto diacylglycerol:acyltransferase which involves the selective synthesis of triacylglycerols may have an ability for suppressing accumulation of triacylglycerols in adipose tissue and blood and may be effective for the therapy of these diseases.

Under the circumstances, it is believed to be worthwhile in the therapy of obesity and hyperlipidemia and of degenerative diseases, such as arteriosclerosis and so on, originated thererfrom, to provide a substance having an activity of inhibiting diacylglycerol:acyltransferase.

Furthermore, it is also expected that a substance having an activity of inhibiting sphingomyelinase which causes hydrolysis of sphingomyelin, a biomembrane constituting lipid, may be useful as a drug for anti-arteriosclerosis, antithrombosis and antiinflammation and as an immunosuppresant, based on a novel functional mechanism not found heretofore.

Means for Solving Problem

The inventors had conducted researches for metabolic products produced by microorganisms and found that substances which have activities for inhibiting diacylglycerol:acyltransferase and sphingomyelinase were produced in the culture medium on the cultivation of a newly identified fungal strain KF-1040 isolated among sea weed. These active substances capable of inhibiting metabolism of lipids were then isolated from the above-mentioned culture medium and purified, wherefrom the chemical structures thereof were determined as represented by the formulae (I) and (II) given below. Since the substances represented by these formulae (I) and (II) were not known in the past, the inventors have named them as "KF-1040 substance A" and "KF-1040 substance B", respectively, which are referred to totally as the "KF-1040 substance".

The present invention has been completed based on the knowledges given above and it relates to the KF-1040 substance comprising the KF-1040 substance A represented by the following formula (I), namely,

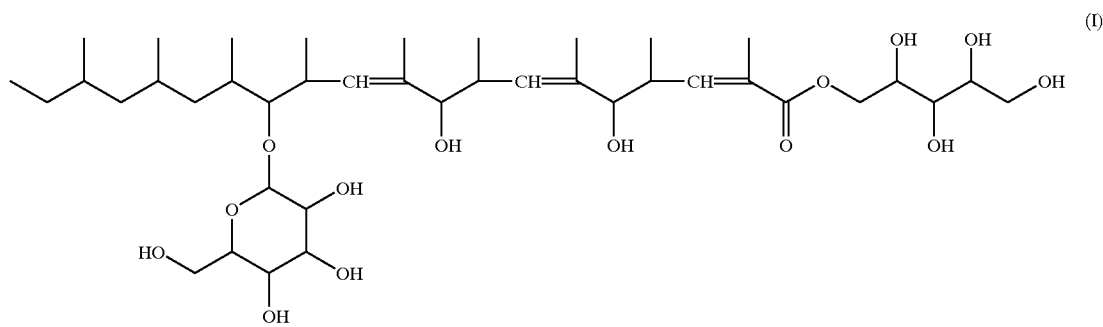

and the KF-1040 substance B represented by the following formula (II), namely,

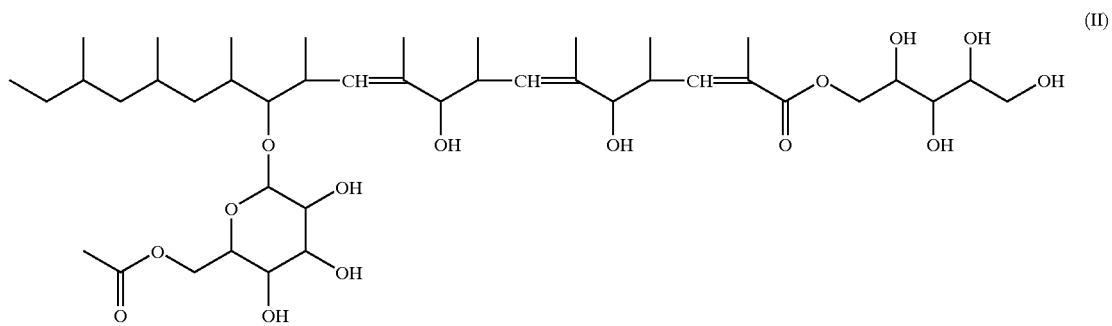

The present invention further relates to a process for producing novel KF-1040 substance comprising culturing a microorganism which belongs to the genus Gliocladium and has an ability of producing KF-1040 substance A and/or KF-1040 substance B in a culture medium, causing to accumulate the resulting KF-1040 substance A and/or KF-1040 substance B in the culture medium and isolating the KF-1040 substance A and/or KF-1040 substance B from the culture medium.

The present invention also relates to a process for producing the KF-1040 substance, wherein the microorganism which belongs to the genus Gliocladium and has an ability of producing KF-1040 substance A and/or KF-1040 substance B is Gliocladium sp. KF-1040(FERM BP-6251). The present invention further relates to a microorganism which belongs to the genus Gliocladium and has an ability of producing KF-1040 substance A and/or KF-1040 substance B.

The microorganism having the ability for producing the KF-1040 substance represented by the formulae (I) and (II)(referred to hereinafter as "KF-1040 material producing fungus") belongs to the genus Gliocladium and, for example, the fungal strain Gliocladium sp. KF-1040 isolated by the inventors is an example to be utilized at the most effectively according to the present invention. The taxonomical properties of this producing strain KF-1040 are as given below:

1. Morphological Properties

This strain grows relatively good in media containing 50% of seawater (with salt concentration of 3.4%), such as potato glucose agar, cornmeal agar, malt extract agar, Miura agar medium and seawater starch agar, with abundance of conidia.

On microscopic observation of colony grown on a cornmeal agar medium, the hypha is transparent and has a septum. The conidiophore assumes both penicillate and verticillate forms. The penicillate conidiophore (having a length of 100–200 μm) erects or branches from the basal hypha and forms at the top end or at the branch several penicillate cyclic phialides of sizes of 2.5–3.0 μm×10–23μm, on which a conidial mass is formed.

On the other hand, the verticillate conidiophore (having a length of 25–50 μm) erects from the basal hypha and forms at the top end or at the branch phialides (of sizes of 3.0–5.0 μm×17–25 μm) of a form of elongate flask or of cone converging toward the top, from which a sole conidial mass is formed. The conidium is colorless and has a shape of ellipsoid or elongate ellipsoid of a size of 2.5–3.0 μm×3.0–5.0 μm, rarely with sharp tip at its one end, for the penicillate conidiophore. For the verticillate, the conidium is colorless and has a ellipsoidal or elongate ellipsoidal form of a size 2.5–3.0 μm×6.0–8.5 μm 2. Cultured Properties on Various Media The results of visual observation of the state of culture of this strain in various culture media at 25° C. for 14 days were as given in the following Table 1.

TABLE 1

| Medium | Growth condition on the medium (diameter of colony) | Color of surface of colony | Color of reverse side of colony | Soluble pigment |
|---|---|---|---|---|
| Potate-glucose agar medium | good (28–30 mm) floccose, flat | bright gray | bright gray | none |
| Cornmeal agar medium | good (24–30 mm) floccose, stripped | bright gray | bright gray | none |
| Malt extract agar medium | good (20–22 mm) floccose, flat | pale gray | bright gray | none |
| Miura agar medium | good (22–24 mm) floccose, ridged a few | bright gray | bright gray | none |
| Seawater starch agar medium | good (24–27 mm) floccose, flat | bright gray | white milky | none |

3. Physiological Properties (1) Optimum Growth Conditions

Optimum growth conditions of the present strain are: pH 4–8, temperature 17–27° C., *seawater concentration 0–50%.

*: salt concentration 3.4% natural seawater is used (2) Growth Condition

Growth range of the strain is: pH 3–10, temperature 9–32° C., *seawater concentration 0–200%

*: salt concentration 3.4% natural seawater is used (3) Nature:Aerobic

As shown in the above, morphological properties, culture condition and physiological properties of the present strain KF-1040 as given above, the inventors carried out comparison of this strain with known fungal strains and reached the identification thereof to be a strain belonging to the genus Gliocladium and named as Gliocladium sp. KF-1040. This strain was deposited on Feb. 6, 1998, at National Institute of Bioscience and Human-Technology, Agency of Industrial Science and Technology, Ministry of International Science and Technology, under the deposition No. FERM P-16629, and was then re-deposited on Feb. 12, 1998, at National Institute of Bioscience and Human-Technology, Agency of Industrial Science and Technology, Ministry of International Science and Technology located at 1–3, Higashi 1-Chome, Tsukuba-shi, Ibaraki-ken, Japan, under the receipt No. FERM BP-6251 from the original deposition by the request for transference to the deposition based on the Budapest Treaty.

As the KF-1040 substance producing fungus to be employed according to the present invention, while the above-mentioned strain Gliocladium sp. KF-1040 is enumerated, every strain which belongs to the genus Gliocladium and produces the KF-1040 substances represented by the formulae (I) and (II) given previously (in the following, referred to integrally as the "KF-1040 substance" so long as not specifically noted),including natural mutants, artificial mutants resulting from irradiation of X-ray and UV ray and by mutational treatment with, such as N-methyl-N'-nitro-N-nitrosoguanidine and 2-aminopurine, fused strains and gene-manipulated strains.

On the practical application of the present invention, the KF-1040 substance producing fungi belonging to the genus Gliocladium is cultured in a culture medium. As the nutrient sources suitable for producing the KF-1040 substance, nutrient medium containing assimilable carbon sources by the microorganism, assimilable nitrogen source by the microorganism and, if necessary, additives including inorganic salts and vitamins are employed. As the carbon source, saccharides, such as glucose, fructose, maltose, lactose, galactose, dextrin and starch, and vegetable oils, such as soybean oil etc., may be incorporated solely or in combination. As the nitrogen source, there may be employed peptone, yeast extract, meat extract, soybean powder, cotton seed powder, corn steep liquor, malt extract, casein, amino acids, urea, ammonium salts and nitrates either solely or in combination. Further, salts, such as phosphates, magnesium salts, calcium salts, sodium salts and potassium salts as well as heavy metal salts, such as iron salts, manganese salts, copper salts, cobalt salts and zinc salts, and vitamins and others adapted to the production of the KF-1040 substance may be added adequately.

Upon the culture, antifoaming agent, based on for example, liquid paraffin, animal oil, vegetable oil, silicone and surfactant, may be added if necessary, when encountered by a severe foaming phenomenon. The cultivation may favorably be carried out usually in a liquid culture medium, while liquid and solid media can be employed so long as the nutrient sources given above are contained. In a small scale production, a culture in a flask may be favorable. For producing the objective material industrially in a large amount, an aerating culture with agitation is preferable, as in other fermentation products.

In case the culture is carried out in a large tank, it is preferable to practice in such a manner that the producing fungus is first inoculated in a relatively small amount of culture medium to cultivate therein, in order to obviate delay of growth of the fungus, and the culture mixture is then transferred to the large tank to effect the production culture therein. Here, it is possible that the culture medium composition is the same with or different from each other for the pre-culture and for the production culture. If necessary, the culture composition may be altered for them.

In case the culture is carried out under the condition of aeration with agitation, techniques including mechanical agitation by impellor or other means, rotation or shaking of the fermenter, pumping agitation and air bubbling may be employed in a pertinent manner. The aeration is carried out under sterilization of air.

The culture temperature may adequately be altered within the range in which the KF-1040 substance producing fungus can produce the KF-1040 substance, while usually the cultivation is carried out at a temperature in the range 20–30° C., preferably at around 27° C. The cultivation is performed usually at a pH of 5–8, preferably at around 7. The duration of cultivation may vary according to each specific culture condition, while 10–20 days are usual.

The KF-1040 substance produced in this manner is present in the thus grown mycelia and in the cultured filtrate. For purifying the KF-1040 substance from the cultured mass, the entire cultured mass is extracted with a water-missible organic solvent, such as acetone, and the extract is subjected to vaccum evaporation to remove the organic solvent, whereupon the resulting residue is extracted with a water-immisible organic solvent, such as ethyl acetate.

In addition to the above-mentioned extraction technique, known practices employed for purifying lipid-soluble substances, such as for example, adsorption chromatography, gel filtration chromatography, thin layer chromatography, centrifugal countercurrent distribution chromatography, high performance liquid chromatography, may be employed in a suitable combination or in repetition to effect separation of the KF-1040 substance into each component substance and to purify it.

The physico-chemical properties of the KF-1040 substance A according to the present invention are as given below:

| | |
|---|---|
| 1) Nature | white powder |
| 2) Molecular weight | 776 (by fast atom bombardment mass spectrometry) |
| 3) Molecular formula | $C_{40}H_{72}O_{14}$ |
| 4) Specific rotation | $[\alpha]_D^{25} = +62°$ (c = 0.1, in methanol) |
| 5) UV absorption maximum (in methanol) | FIG. 1, at 203 nm ($\epsilon$ = 24900), 220 nm ($\epsilon$ = 18000) and 275 nm ($\epsilon$ = 1200) |
| 6) IR absorption maximum (KBr tablet) | FIG. 2, at 1637 cm$^{-1}$ and 3434 cm$^{-1}$ |
| 7) Proton NMR spectrum (in heavy hydrogen methanol) | as shown in FIG. 3 |
| 8) $^{13}$C-NMR spectrum (in heavy hydrogen methanol) | as shown in FIG. 4 |
| 9) Solubility in solvents | solule in methanol, benzene, chloroform and ethyl acetate; slightly soluble in water and hexane |
| 10) Color reaction | positive to sulfuric acid and to phosphorus molybdic acid |
| 11) Acidic or alkaline nature | neutral |

Under the examination of the physico-chemical properties, spectral analyses data of the KF-1040 substance A as given above, the chemical structure of the KF-1040 substance A was determined to be as represented by the following formula (I):

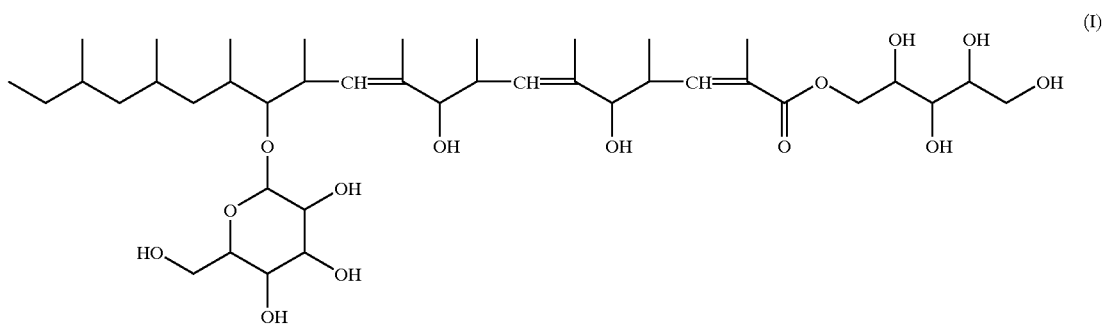

(I)

The physico-chemical properties of the KF-1040 substance B according to the present invention are as given below:

| | |
|---|---|
| 1) Nature | white powder |
| 2) Molecular weight | 818 (by fast atom bombardment mass spectrometry) |
| 3) Molecular formula | $C_{42}H_{74}O_{15}$ |
| 4) Specific rotation | $[\alpha]_D^{25} = +120°$ (c = 0.1, in methanol) |
| 5) UV absorption maximum (in methanol) | FIG. 5 at 204 nm ($\epsilon$ = 43000), 218 nm ($\epsilon$ = 30300) and 272 nm ($\epsilon$ = 2900) |
| 6) IR absorption maximum (KBr tablet) | FIG. 6, at 1633 $cm^{-1}$ and 3417 $cm^{-1}$ |
| 7) Proton NMR spectrum (in heavy hydrogen methanol) | as shown in FIG. 7 |
| 8) $^{13}$C-NMR spectrum (in heavy hydrogen methanol) | as shown in FIG. 8 |
| 9) Solubility in solvents | soluble in methanol, benzene, chloroform and ethyl acetate; slightly soluble in water and hexane |
| 10) Color reaction | positive to sulfuric acid and to phosphorus molybdic acid |
| 11) Acidic or alkaline nature | neutral |

Under the examination of the physico-chemical properties, spectral analyses data of the KF-1040 substance B as given above, the chemical structure of the KF-1040 substance B was determined to be as represented by the following formula (II):

Now, the description is directed to the biological nature of the KF-1040 substance A and KF-1040 substance B.

(1) Inhibitory Action to Rat-originated Diacylglycerol:Acyltransferase

The activity of diacylglycerol:acyltransferase was determined by the modified method of Mayorek and Bar-Tana [J. Biol. Chem., 260, 6528–6532 (1985)].

Thus, a microsomal fraction prepared from rat liver was used as the enzyme source. To a 175 mM Tris-HCl buffer (pH 8.0) containing 8 mM of $MgCl_2$, 1 mg/ml of bovine, serum albumin and 2.5 mM of diisopropyl fluorophosphate, there were added 0.75 mM of dioleoylglycerol and 30 μM of [1-$^{14}$C]-palmitoyl-CoA (0.02 μCi) and the total volume was adjusted to 200 μl, whereupon the enzymatic reaction mixture was incubated at 23° C. for 15 minutes. The total lipids were extracted with chloroform/methanol mixture and each lipid was separated by a TLC (with Kieselgel $GF_{254}$ and a developer of petroleum ether/diethyl ether/acetic acid of 80/20/1), followed by determination of the radioactivity of the triacylglycerol fraction using RADIOSCANNER (of the firm AMBIS System Inc.) to determine the diacylglycerol:acyltransferase activity.

The calculation of the drug concentration corresponding to 50% inhibition of this enzyme gives the values of 16 μg/ml for the KF-1040 substance A and 9.0 μg/ml for the KF-1040 substance B.

(2) Inhibitory Action to Formation of Triacylglycerol in Human-originated Cells (Raji Cell Originated from Human Burkitt Lymphoma)

The assessment of influence of the substances on the triacylglycerol formation was performed in accordance with

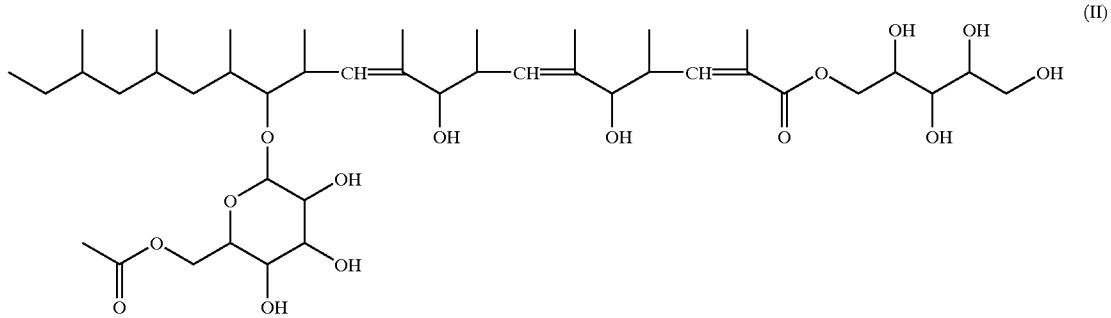

(II)

While the description in the above has been directed to the details of various physico-chemical properties of the KF-1040 substance A and of the KF-1040 substance B, it is recognized that any compound having properties corresponding to the above-identified properties has not been reported in the literature. Therefore, it is decided that the KF-1040 substances are novel substances.

the method of Tomoda et al [J. Biol. Chem., 266, 4214–4219 (1991)] using human-originated cells (Raji cell originated from human Burkitt lymphoma).

A Raji cell dispersion of $2.7 \times 10^6$ cells per milliliter containing 0.36 nM [1-$^{14}$C]-oleic acid (0.02 μCi) in the presence or absence of the; substance was filled up to a total volume 200 μl, whereupon the reaction was caused at 37° C. for 30 minutes. The total lipids were extracted with chloroform/methanol (2/1) mixture. The subsequent procedures were carried out in the same manner as in the above experiment (1) "inhibitive action to rat-originated diacylglycerol-acyltransferase".

The calculation of the drug concentration corresponding to 50% inhibition of triacylglycerol formation gives the values of 10 µg/ml for the KF-1040 substance A and 10 µg/ml for the KF-1040 substance B.

(3) Inhibitory Action to Rat Brain-originated Neutral Sphingomyelilnase

The assessment of influence of the substances on the neutral sphingomyelinase originated from rat brain was performed in accordance with the modified method of Murakami & Arima [J. Neurochem., 52, 611–618 (1989)].

Thus, a membrane fraction prepared from a rat brain was used as the enzyme source and thereto were added 20 mM of HEPES-NaOH buffer solution (pH 7.4), 6.5 mM of $MgCl_2$, 0.1% Triton X-100 and 25 µM [N-methyl-$^3$H]-sphingomyelin (0.006 µCi) and the mixture was filled up to a total volume of 50 µl. After the reaction at 37° C. for 30 minutes, 200 µl of chloroform/methanol mixture (1/2 volume ratio) were added to the reaction mixture to separate the reaction product [$^3$H]-phosphocholine from the starting material [$^3$H]-sphingomyelin. The supernatant layer was taken up into a 50 µl vial. The amount of [$^3$H]-phosphocholine was quantitatively determined by a liquid scintillation counter to estimate the neutrtal sphingomyelinase activity.

The calculation of the concentration of the KF-1040 substance corresponding to 50% inhibition of this enzyme gives the values of 4.2 µg/ml for the KF-1040 substance A and 6.1 µg/ml for the KF-1040 substance B.

(4) Influence on Human Placenta-Originated Acid Sphingomyelinase

The assessment of influence of the substances on human placenta-originated acidic sphingomyelinase was performed in accordance with the method of Jones et al [Biochem. Journal, 195, 373–382 (1981)] with partial modification.

Thus, an acid sphingomyelinase originated from human placenta (a product of the firm Sigma) was used as the enzyme source and thereto were added 250 mM of sodium acetate buffer solution (pH 5.0), 0.1% of NP-40 (of the firm Sigma), 25 µM [N-methyl-$^3$H]-sphingomyelin (0.006 µCi) and various concentrations of the substance, and the mixture was filled up to a total volume of 50 µl. After the reaction at 37° C. for 30 minutes, 200 µl of chloroform/methanol mixture (1/2 volume ratio) was added to the reaction mixture to separate the reaction product [$^3$H]-phosphocholine from the starting material [$^3$H]-sphingomyelin. The supernatant layer was taken up into a 50 µl vial. The amount of [$^3$H]-phosphocholine was quantitatively determined by a liquid scintillation counter to estimate the acid sphingomyelinase activity.

The calculation of the concentration of the KF-1040 substance corresponding to 50% inhibition of this enzyme gives the values of 48 µg/ml for the KF-1040 substance A and 24 µg/ml for the KF-1040 substance B.

As described above, the novel substance according to the present invention exhibits activity for inhibiting diacylglycerol:acyltransferase and sphingomyelinase and, hence, is useful for the prophylaxis and therapy of patients with diseases relating to arterisclerosis, obesity, thrombosis, inflammations and immunofunctional disorder.

EXAMPLE

Figure 1:
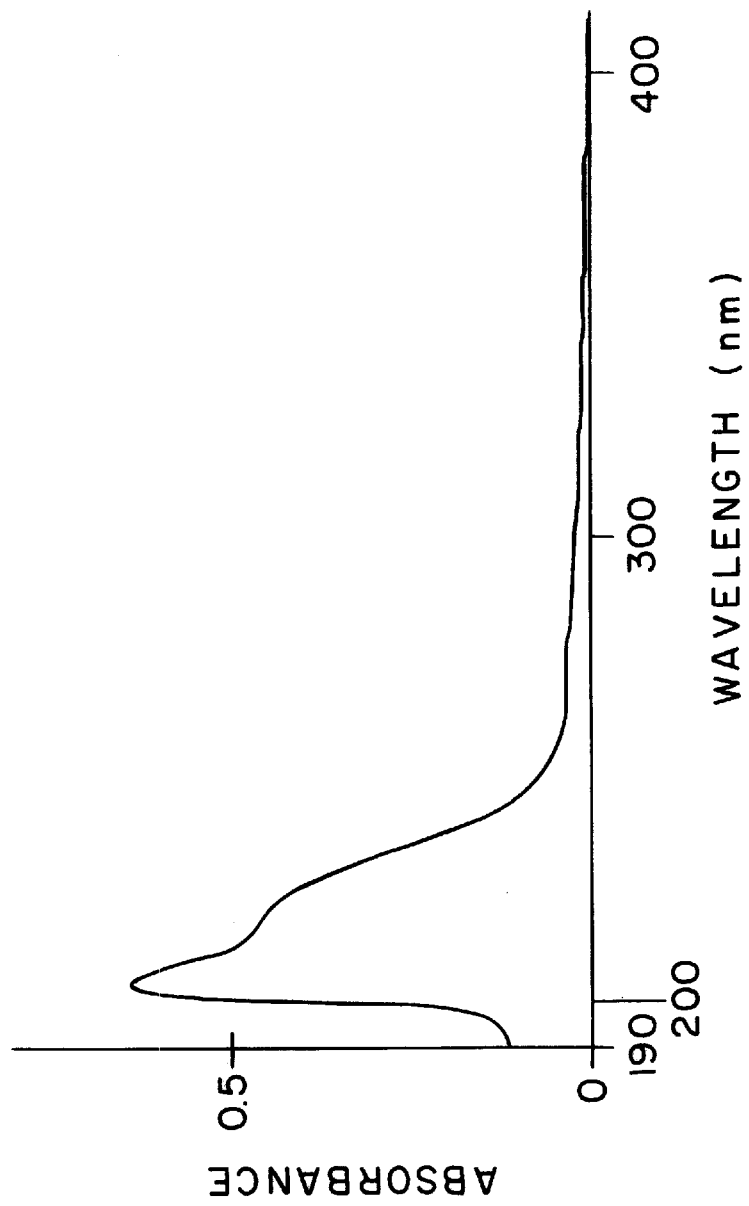
FIG. 1 shows the UV absorption spectrum (in methanol) of the KF-1040 substance A according to the present invention.
Figure 2:
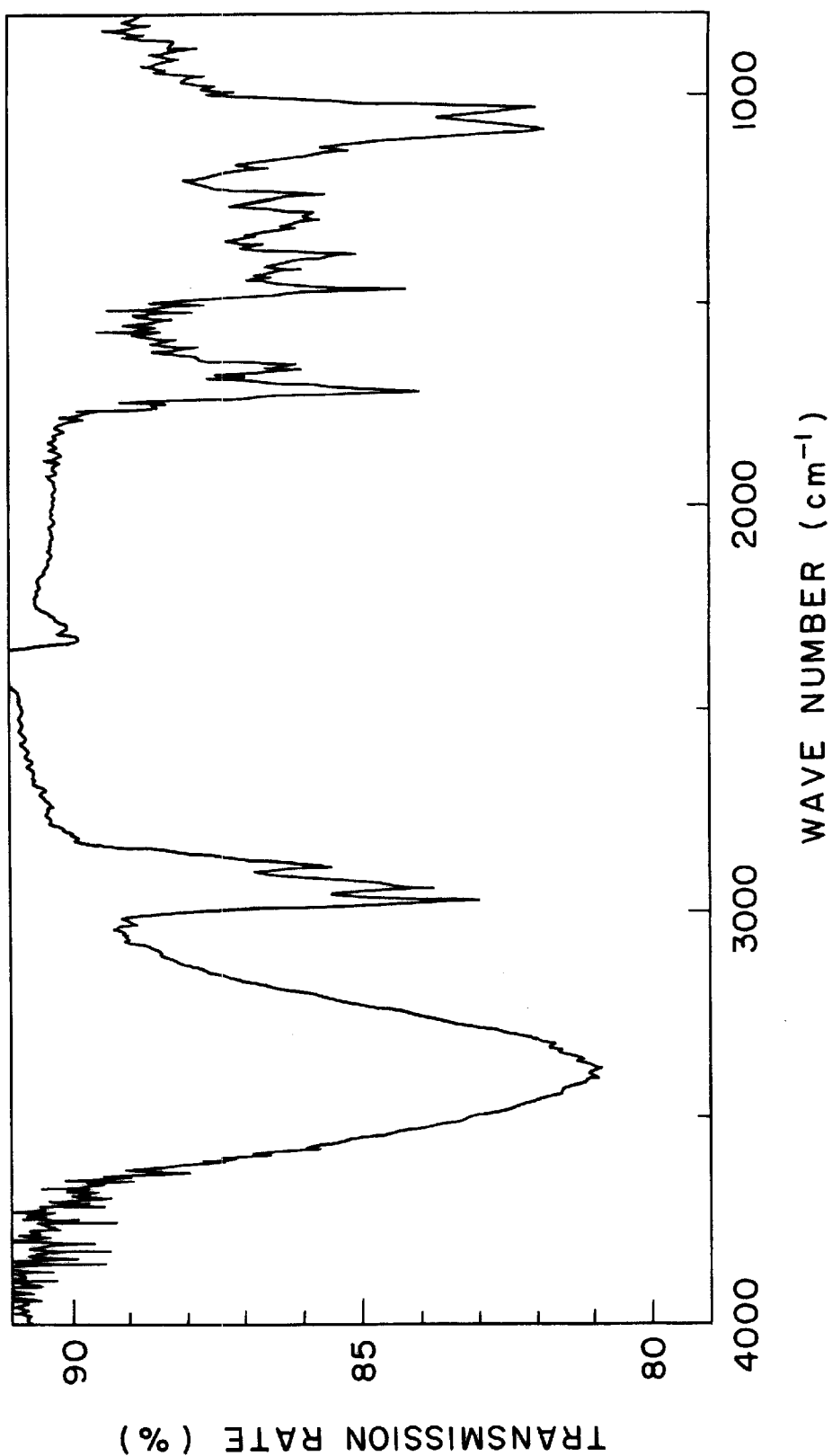
FIG. 2 shows the IR absorption spectrum (with KBr) of the KF-1040 substance A according to the present invention.
Figure 3:
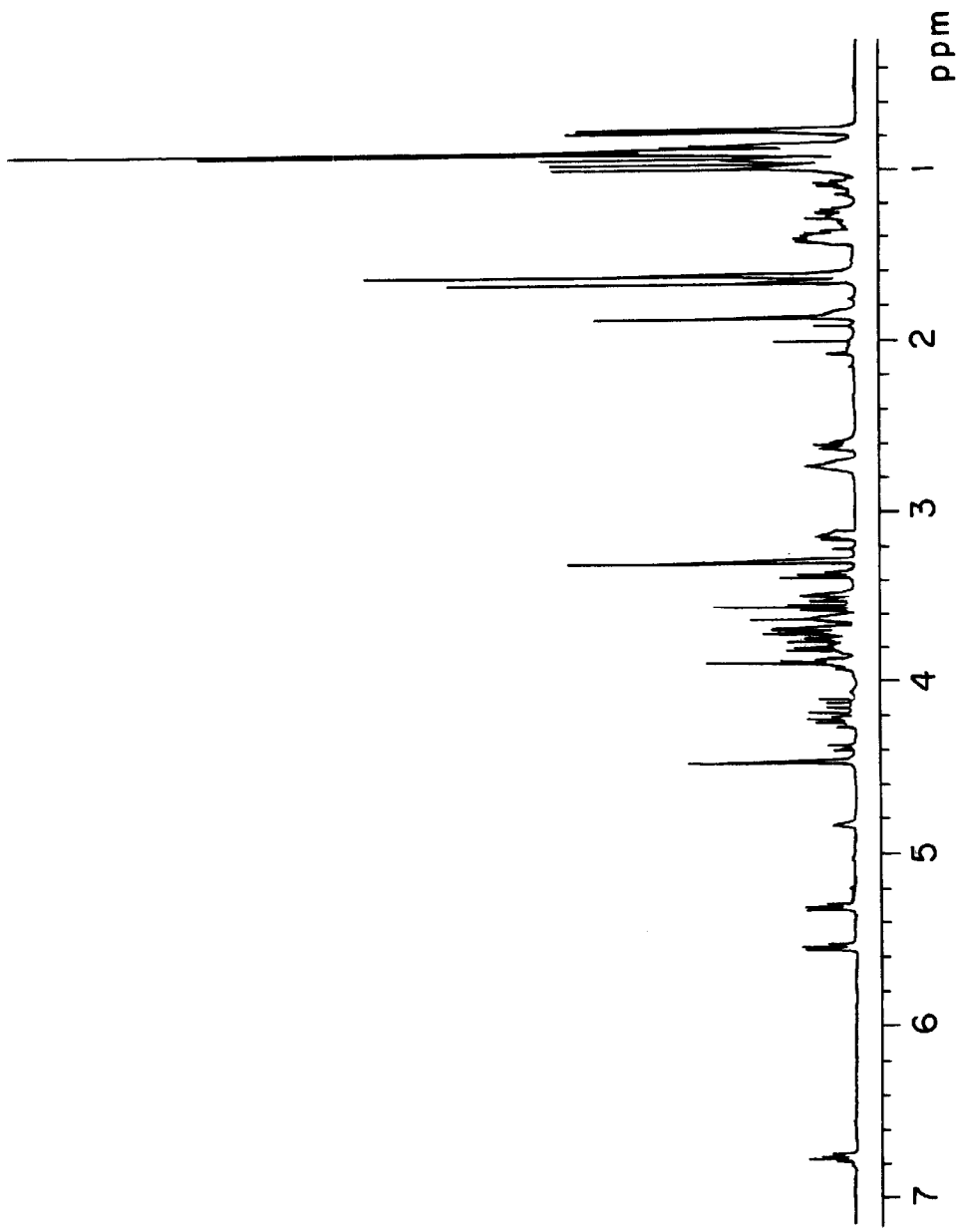
FIG. 3 shows the proton NMR spectrum (in heavy methanol) of the KF-1040 substance A according to the present invention.
Figure 4:
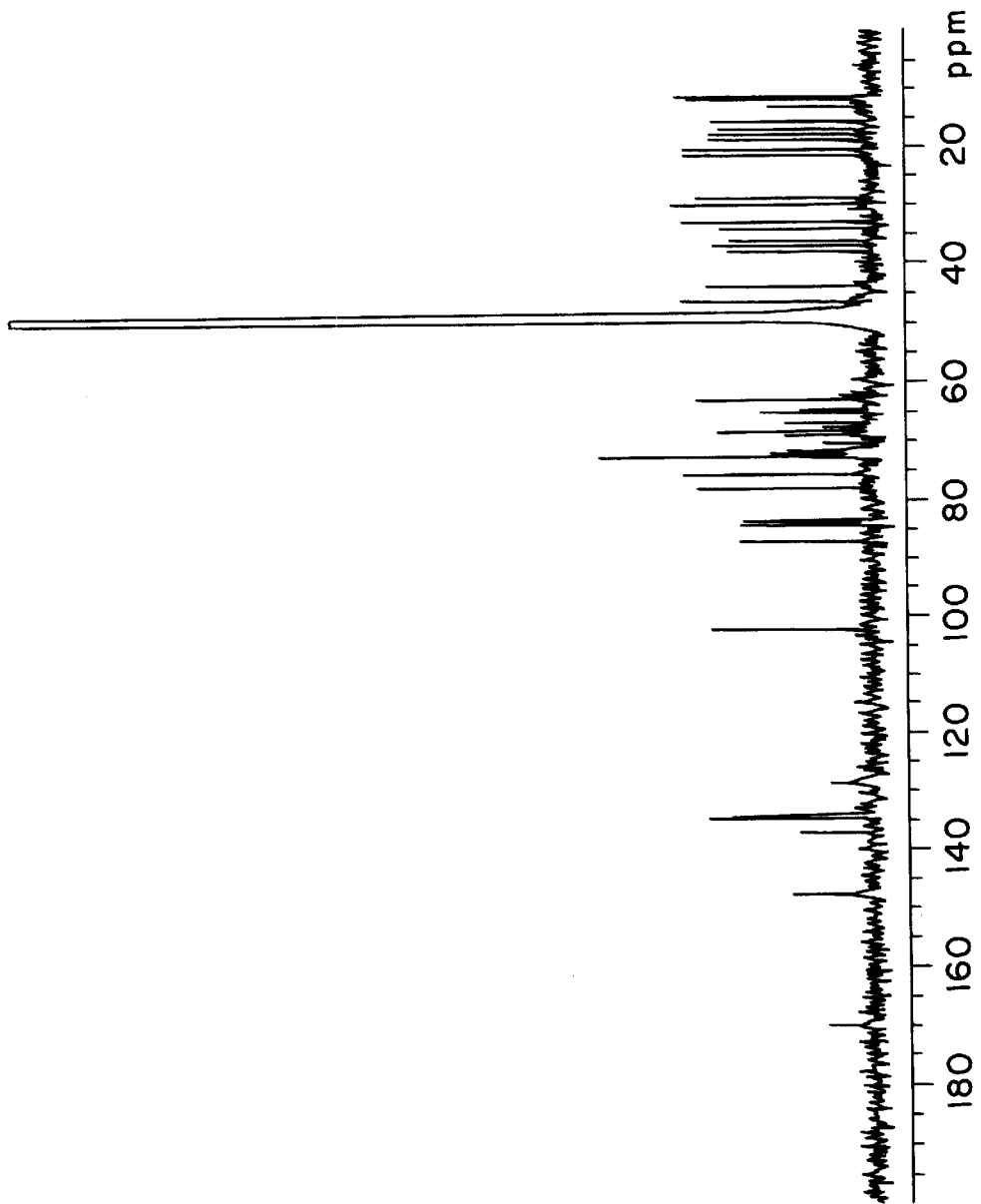
FIG. 4 shows the $^{13}$C-NMR spectrum (in heavy methanol) of the KF-1040 substance A according to the present invention.
Figure 5:
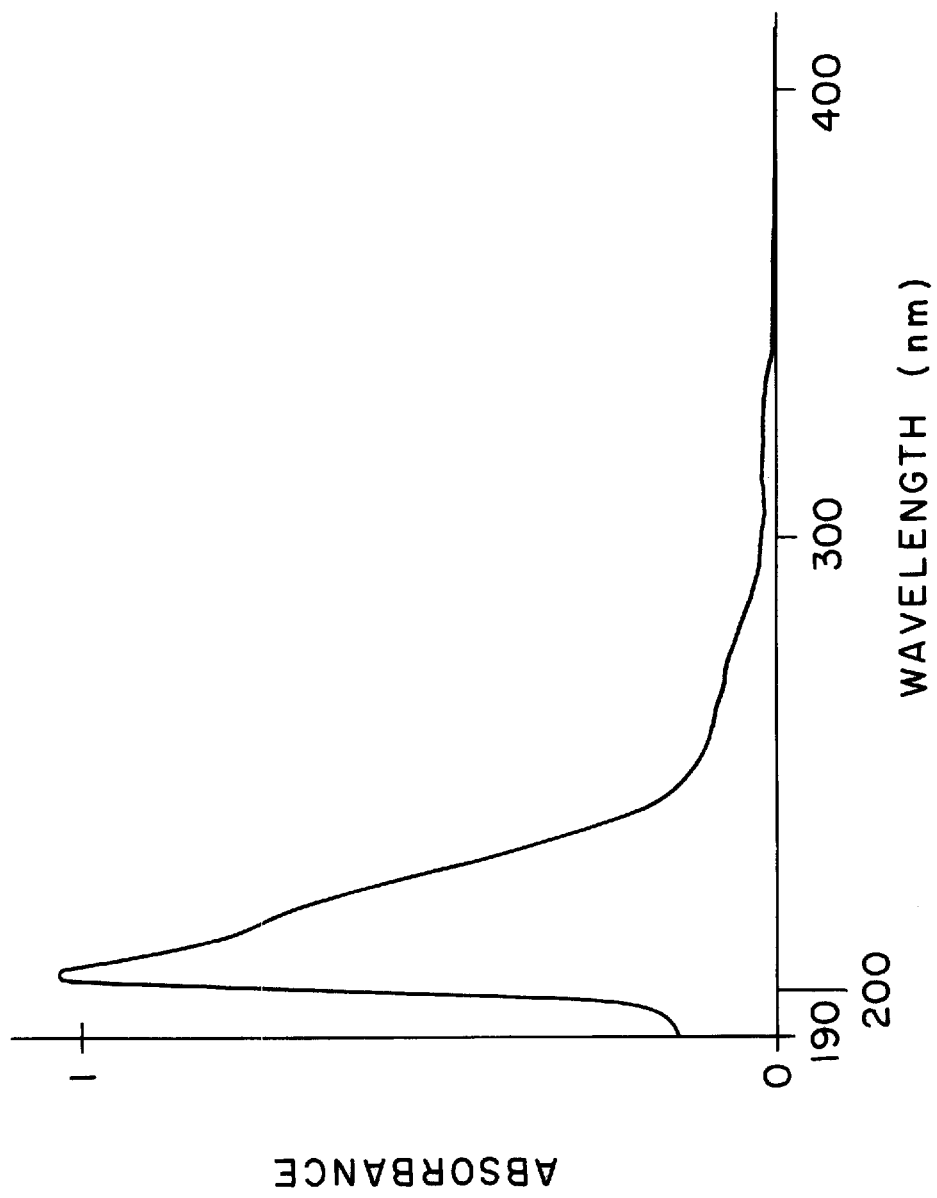
FIG. 5 shows the UV absorption spectrum (in methanol) of the KF-1040 substance B according to the present invention.
Figure 6:
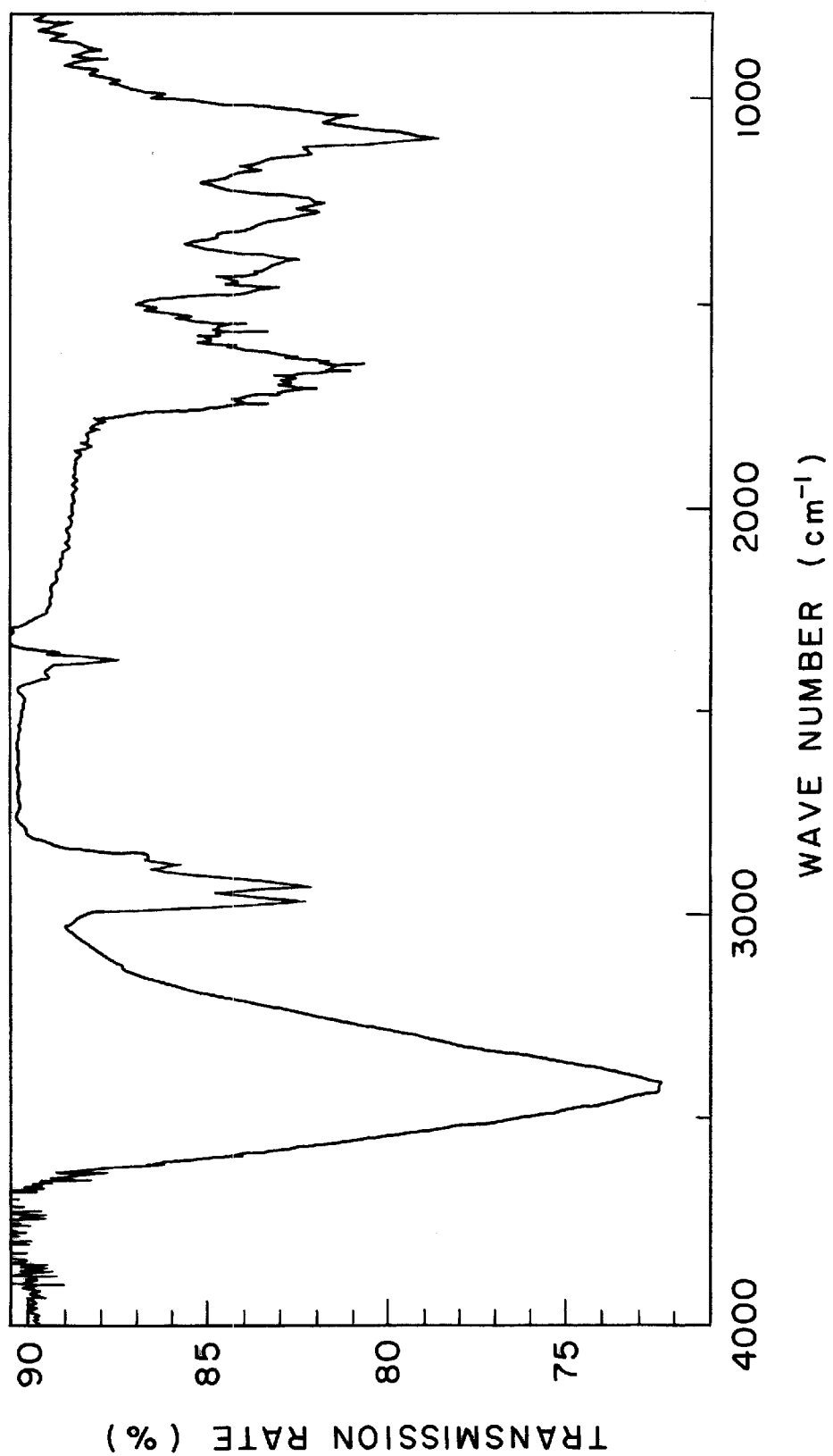
FIG. 6 shows the IR absorption spectrum (with KBr) of the KF-1040 substance B according to the present invention.
Figure 7:
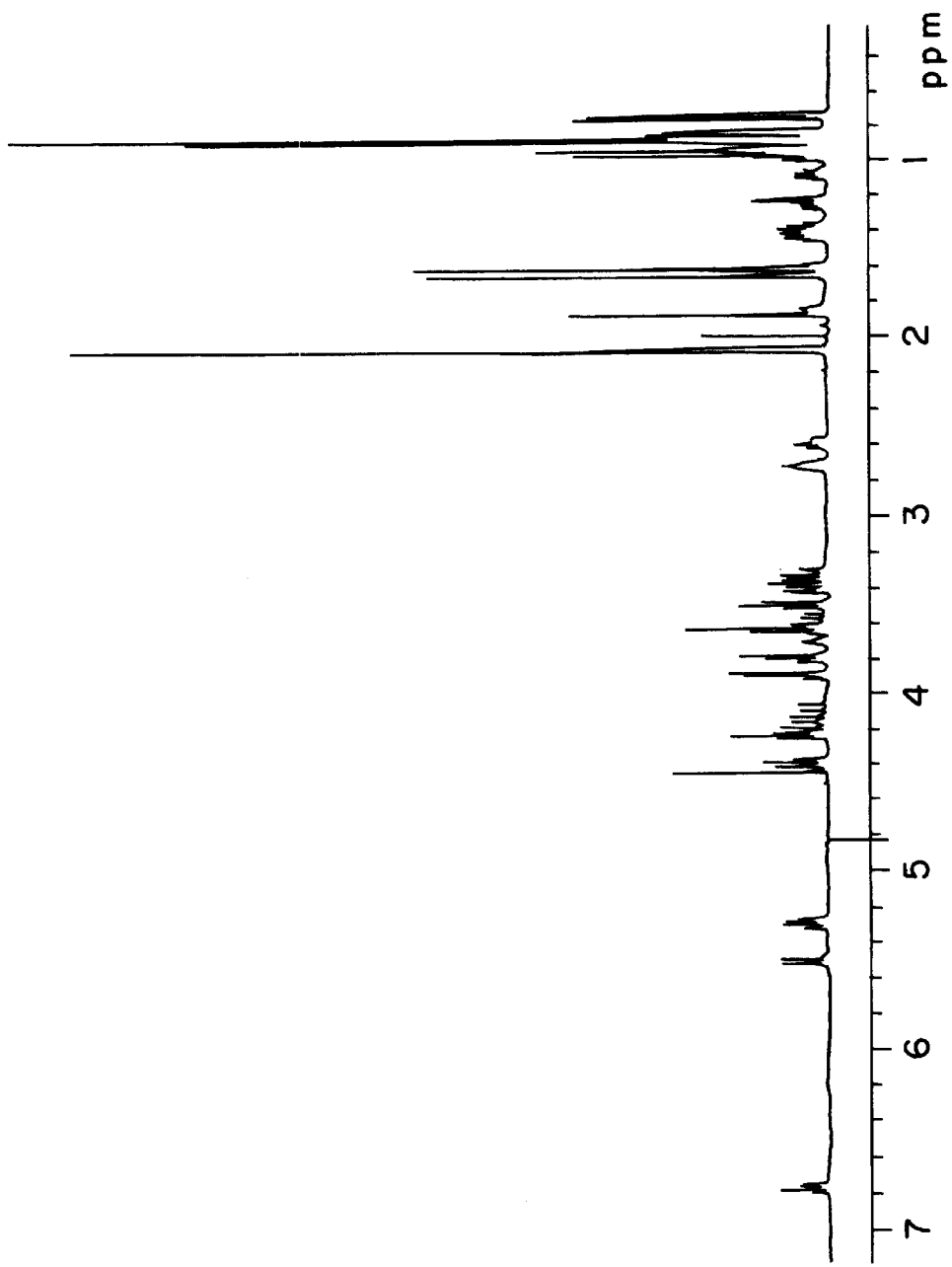
FIG. 7 shows the proton NMR spectrum (in heavy methanol) of the KF-1040 substance B according to the present invention.
Figure 8:
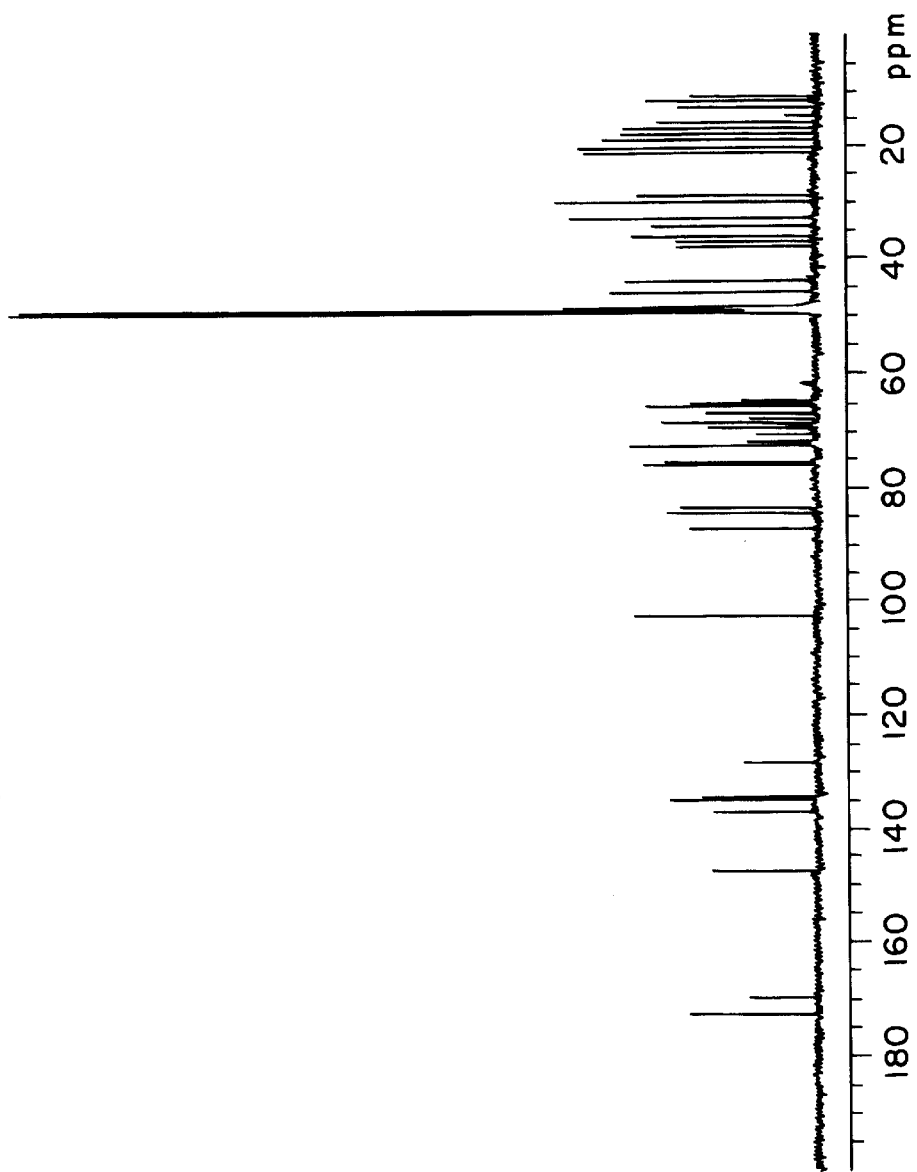
FIG. 8 shows the $^{13}$C-NMR spectrum (in heavy methanol) of the KF-1040 substance B according to the present invention.

Two 500-ml Erlenmeyer flasks charged each with 100 ml of a liquid culture medium (pH 6.0) prepared by dissolving 2.0% of glucose, 0.5% of polypeptone (of Nippon Seiyaku K. K.), 0.2% of yeast extract (of Oriental Kobo Kogyo K. K.), 0.05% of magnesium sulfate 7 hydrate, 0.1% of potassium dihydrogen phosphate and 0.1% of agar in 50% of natural seawater were inoculated each with one loopful of the strain of Gliocladium sp. KF-1040 (FERM BP-6251) whereupon each inoculated medium was cultured at 27° C. for 4 days with shaking.

The resulting cultured medium was used as the cultured seed. 60 Roux flasks of each 1,000 ml capacity were charged each with 300 ml of a liquid culture medium (pH 6.0) prepared by dissolving 100 g/l of potate and 1.0% of glucose in 50% of natural seawater. After sterilization and cooling, each flask was inoculated aseptically with 3 ml of the culture seed and the inoculated mixture was cultured at 27° C. for 16 days under standing still.

To the total cultured liquor, 18 litters of acetone were added and agitated well, followed by concentration under a reduced pressure and the so-concentrated liquor was extracted with ethyl acetate. The extract layer was subjected to concentration under a reduced pressure, whereby 2.2 grams of a crude product were obtained. This crude product was dissolved in a small amount of acetonitrile and the resulting solution was passed to an ODS column (200 g, supplied from Senshu Kagaku K. K., ODS-SS-1020T) filled with a 30% acetonitrile water. After washing the column with 50% acetonitrile water, the column was eluted with 60% acetonitrile water and, then, with 70% acetonitrile water. From the eluates, 87 mg of a crude product of the substance A and 104 mg of a crude product of the substance B were obtained by concentration under reduced pressure.

Each of the crude products was fractionated by a high performance liquid chromatography (Shiseido Capsulepack, ODS-SG column, 20 mm×250 mm, flow rate=6.0 ml/min.; detection: 215 nm UV using an eluent of 70% acetonitrile water). A fraction eluted at the retention time of 17 minute for the substance A and a fraction eluted at the retention time of 23 minute for the substance B were collected, respectively. Each fraction was treated by removing the organic solvent and extracting the aqueous layer with ethyl acetate, whereby 16 mg of the KF-1040 substance A and 40 mg of the KF-1040 substance B were obtained.

EFFECT OF THE INVENTION

As detailed above, the novel KF-1040 substance according to the present invention exhibits activity for inhibiting diacylglycerol:acyltransferase and sphingomyelinase and, hence, is expected to be useful for the prophylaxis and therapy of patients with diseases relating to arteriosclerosis, obesity, thromobosis, inflammations and immunofunctional disorder.

What is claimed is:

1. KF-1040 substance comprising KF-1040 substance A represented by the following formula (I), namely,

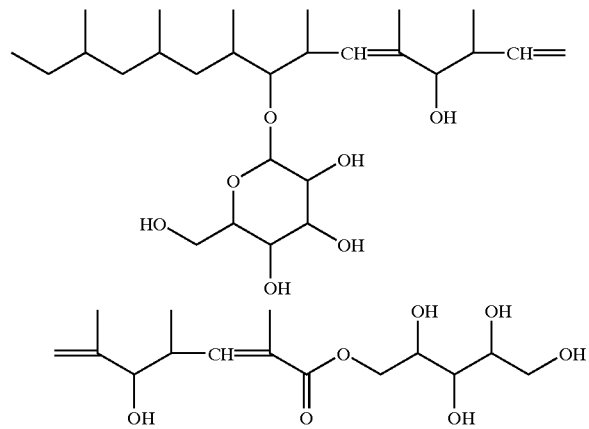

and KF-1040 substance B represented by the following formula (II), namely,

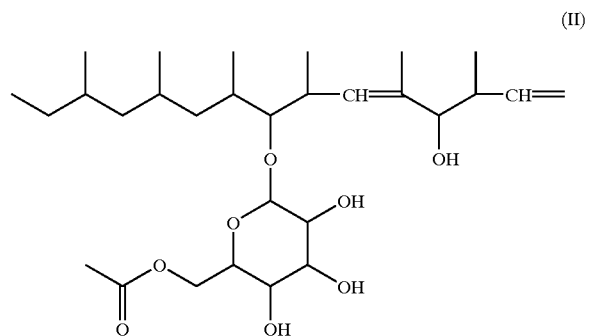

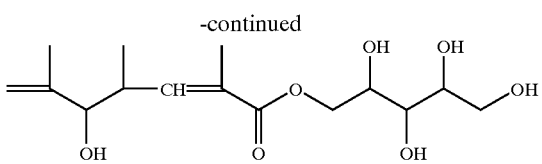

2. A process for producing KF-1040 substance as defined in claim 1, comprising cultivating a microorganism Gliocladium sp. KF-1040, said microorganism having an ability of producing KF-1040 substance A and/or KF-1040 substance B in a culture medium, causing the resulting KF-1040 substance A and/or KF-1040 substance B to accumulate in the culture medium and harvesting the KF-1040 substance A and/or KF-1040 substance B from the culture medium.

3. An isolated culture of a microorganism Gliocladium sp. KF-1040, said microorganism having an ability of producing KF-1040 substance A and/or KF-1040 substance B.

4. The process for producing KF-1040 substance according to claim 2, wherein said culture medium comprises seawater.

5. The process for producing KF-1040 substance according to claim 4, wherein said seawater has a salt concentration of 3.4%.

6. The process for producing KF-1040 substance according to claim 2, wherein said culture medium comprises 50% of seawater.

7. The process for producing KF-1040 substance according to claim 2, wherein said microorganism is grown in an aerated and agitated culture medium.

8. The process for producing KF-1040 substance according to claim 2, wherein said microorganism has been isolated from seaweed.

9. The isolated culture of a microorganism according to claim 3, wherein said microorganism has been isolated from seaweed.

* * * * *